United States Patent [19]
Nagy et al.

[11] Patent Number: 5,223,413
[45] Date of Patent: Jun. 29, 1993

[54] PROCESS FOR THE PREPARATION OF VANCOMYCIN

[75] Inventors: Mariann Nagy; Miklós Járai; István Financsek; Ilona Varga; Géza Kocsis; Viola Muri; Andrási András; László Kégl, all of Budapest; Gabriella Zlatos, SZentendre; Márta Szóke née Zlatos, Budapest; Endre Kollár, Budapest; Agnes Udvardy, Budapest; Mihály Garamvölgyi, Debrecen, all of Hungary

[73] Assignee: Biochin Biotechnologial Leanyvallalat, Budapest, Hungary

[21] Appl. No.: 768,444
[22] PCT Filed: Nov. 27, 1990
[86] PCT No.: PCT/HU90/00079
§ 371 Date: Sep. 26, 1991
§ 102(e) Date: Sep. 26, 1991
[87] PCT Pub. No.: WO91/08300
PCT Pub. Date: Jun. 13, 1991

[30] Foreign Application Priority Data

Nov. 27, 1989 [HU] Hungary ............... 6184/89

[51] Int. Cl.$^5$ ............... C12P 21/04; C12P 19/44; C12R 1/29
[52] U.S. Cl. ............... 435/71.3; 435/74; 435/75; 435/252.1; 435/803; 435/822; 435/867
[58] Field of Search ............... 435/252.1, 71.3, 822, 435/867, 803, 74, 75

[56] References Cited

U.S. PATENT DOCUMENTS

| 3,067,099 | 12/1962 | McCormick et al. | 435/72 |
| 4,548,924 | 10/1985 | Michel | 514/10 |
| 4,549,925 | 10/1985 | Higgins et al. | 514/10 |
| 4,558,008 | 12/1985 | Boeck et al. | 435/75 |
| 4,558,009 | 12/1985 | Boeck et al. | 435/75 |
| 4,845,194 | 7/1989 | Glass et al. | 435/71.3 |
| 4,868,285 | 9/1989 | Wall | 435/71.3 |
| 4,918,054 | 4/1990 | Haneishi et al. | 514/8 |
| 4,946,941 | 8/1990 | Kondo et al. | 435/71.3 |

*Primary Examiner*—Herbert J. Lilling
*Attorney, Agent, or Firm*—Keil & Weinkauf

[57] ABSTRACT

The invention relates to a process for preparation of the vancomycin antibiotic in a microbiological way by aerobic fermentation, by using a strain belonging to the Micropolyspora species in a culture-medium containing assimilable carbon and nitrogen sources as well as mineral salts. According to the invention as microorganisms the aminoglycoside-resistant NCAIM 001092 and NCAIM 001093 mutants of the strain belonging to the *Micropolyspora orientalis* species are used. Nitrates are suitable mineral salts in the fermentation. Soy flour, glycerol, calcium gluconate, starch are useful carbon sources. The fermentation is carried out preferably at a temperature of 29°–30° C. The vancomycin antibiotic produced in the fermentation is separated by using reverse osmosis and ultrafiltration following ion-exchange chromatography.

2 Claims, No Drawings

PROCESS FOR THE PREPARATION OF VANCOMYCIN

The invention relates to a process for preparation of the vancomycin antibiotic in a microbiological way by an aerobic fermentation, by using an aminoglycoside-resistant mutant of a strain belonging to the *Micropolyspora orientalis* species on a culture-medium containing assimilable carbon and nitrogen sources as well as mineral salts.

Vancomycin is a glycopeptide-type antibiotic produced by strains belonging to the *Micropolyspora orientalis* species. In earlier systematic classifications these strains had been mentioned under the names *Streptomyces orientalis* and *Nocardia orientalis*, respectively [M. Goodfellow et al.: The Biology of Actinomycetes, Academic Press Inc. Ltd., London, page 129 (1984)]. This property of both of the above strains was first the described in U.S. Pat. No. 3,067,099.

For preparing vancomycin on an industrial scale, *Micropolyspora orientalis* microorganism is grown in a culture-medium containing assimilable carbon and nitrogen sources as well as mineral salts under aerobic conditions, then the antibiotic produced during the fermentation is separated from the fermentation broth (see e.g. U.S. Pat. Nos. 4,400,753 and 4,667,024).

It is known that the vancomycin antibiotic structurally consists of two essential moieties: a sugar unit, chemically $\alpha$-O-vancosamine-$\beta$-O-glucosyl and a heptapeptide unit which is a so-called pseudopeptide and not a genuine one. This distinction is important because in the microorganisms genuine peptides and proteins are synthetized on the surface of the so-called ribosomes, in a protein-synthetizing system being practically identical in all living organisms; whereas the pseudopeptide-type secondary metabolite products are produced not in the above system but on the surfaces of complex enzymes being independent from the ribosomes. The ribosomes, i.e. the "normal" protein-synthetizing systems of the cells are built up from ribosomal ribonucleic acids and proteins. It is also known that aminoglycoside-type antibiotics such as e.g. streptomycin, kanamycin, neomycin and gentamycin act on microorganisms sensitive to them in such a way that, being bound to specific sites of the ribosomal ribonucleic acids, they prevent the development of ribosomes having a structure necessary for the "normal" protein synthesis. In microorganisms, which are resistant to the aminoglycoside antibiotics, the structures of ribosomal ribonucleic acids building up the ribosomes are altered in such a manner that the binding of aminoglycosides is inhibited, whereby they cannot influence the ribosomal structure and become inactive.

Since the pseudopeptide-type secondary metabolic products are synthetized not on the ribosomes but on the surfaces of complex enzymes which are independent from the ribosomes and do not contain ribosomal ribonucleic acids, aminoglycoside-type antibiotics have substantially no effect on these enzymes. Indeed, no data or observations are found in the literature which would give any evidence of aminoglycoside-induced alteration of the non-ribosomal peptide or pseudopeptide synthesis.

The yields of known processes for the preparation of vancomycin are rather low.

Thus, it was aimed to develop a process resulting in a higher productivity in comparison to the earlier ones and to isolate novel strains for this purpose.

In the course of our inventigations the *Micropolyspora orientalis* NCAIM 001091 strain producing the vancomycin antibiotic was subjected to a mutagenic effect, then aminoglycoside-resistant mutants were isolated. The mutagenization was carried out according to the literature by using N-methyl-N'-nitro-N-nitrosoguanidine or UV irradiation as mutagenic agents. Other known mutagenic agents, e.g. radioactive irradiation or nitrogen mustards etc. may also be used.

It has surprisingly been observed after the mutagenic treatment that, among the streptomycin- and kanamycin-resistant colonies grown on a selective culture-medium containing streptomycin and kanamycin, a great number of colonies were found with a significantly higher vancomycin-producing capability in comparison to that of the original strain. Two of the progeny strains, V-1 and V-2 showing the most favourable properties from the viewpoint of an industrial fermentation were deposited at the National Collection of Agricultural and Industrial Microorganisms, H-1502 Budapest PF53, Hungary (recognized as an international depositary authority under the Budapest Treaty) on Jul. 12, 1989 under the numbers NCAIM 001092 and NCAIM 001093, respectively.

Our observations are summarized in the following Table.

| | Number of colonies isolated | Vancomycin-productivity in relation of the starting strain % | | | |
|---|---|---|---|---|---|
| | | 70–80% | 80–120% | 120–150% | above 150% |
| Mutagenic treatment, then spreading on a medium containing streptomycin | 361 | 48 | 293 | 18 | 2 |
| Mutagenic treatment, then spreading on a medium containing kanamycin | 295 | 54 | 224 | 16 | 1 |
| Mutagenic treatment, then spreading on a non-selective medium | 321 | 59 | 261 | 1 | — |

The composition of the selective culture-medium (sign: VS-1) is as follows:

| | |
|---|---|
| Soluble starch | 10 g |
| Glucose | 5 g |
| Tripcasin (Manufactured by: Institute for Serobacteriological Production and Research HUMAN, Hungary) | 3 g |
| Difco yeast extract | 4 g |
| Calcium carbonate | 1 g |
| Agar | 15 g |
| Distilled water | up to 1000 ml. |

The pH value is adjusted to 7.0 by adding sulfuric acid before autoclaving.

Streptomycin and kanamycin are used in a concentration of 1000 $\mu$g/ml in the culture-medium.

Instead of the VS-1 medium the commonly known and usual Czapek-Dox culture-medium may also be used.

An advantageous property of the NCAIM 001092 and NCAIM 001093 strains and their progeny strains resides therein that they utilize well raw materials of industrial grade used as carbon sources such as corn, wheat and potato starch, dextrin, saccharose, glucose, glycerol, calcium gluconate and corn, potato and wheat starch liquefied by amylase; whereas they utilize soy flour, corn steep liquor, protein hydrolysates such as meat extract, casein hydrolysate and yeast extracts as well as ammonium and nitrate salts as nitrogen sources.

Thus, e.g. a fermentation medium (sign: VF-2) with the following composition may preferably be employed:

| | |
|---|---|
| Glycerol | 60 g |
| Soy flour | 20 g |
| Calcium gluconate | 12 g |
| Potassium dihydrogen phosphate | 0.2 g |
| Magnesium chloride | 0.2 g |
| Calcium carbonate | 3.0 g |
| Tap water | up to 1000 ml. |

For a laboratory fermentation 50 ml of VF-2 culture-medium are used in a flask of 500 ml volume.

It has been observed during our investigations that another preferable property of the NCAIM 001092 and NCAIM 001093 strains and their progeny strains is that the production of vancomycin is significantly increased in fermentations carried out in a culture-medium containing soy flour as nitrogen source when nitrate salts are added to the culture medium at the beginning of the fermentation. Thus, e.g. on adding sodium nitrate or potassium nitrate salts in an amount of 0.1-2.5%, preferably 0.6-1.0% to the VF-2 culture-medium in addition to the components listed above, the vancomycin production at the end of fermentation is by 30-40% higher in comparison to that obtained in the culture-medium with the same composition but without nitrate content.

Thus, according to the invention the vancomycin antibiotic is prepared in such a way that aminoglycoside-resistant mutants of the NCAIM 001091 strain belonging to the *Micropolyspora orientalis* species, preferably the NCAIM 001092 and NCAIM 001093 strains are grown on a culture-medium containing assimilable carbon source such as corn-, potato-, wheat starch and/or corn-, potato-, wheat starch liquefied by amylase and/or glycerol and/or glucose and/or dextrin and/or saccharose and/or calcium gluconate as well as assimilable nitrogen source, e.g. soy flour and/or corn steep liquor and/or protein hydrolysate such as meat extract yeast extracts, casein hydrolysate as well as mineral salts, preferably nitrate salts, under aerobic conditions at a temperature of 20°-40° C., preferably 30° C., then the antibiotic is separated from the fermentation broth in a known manner.

By using the process according to the invention an antibiotic content of 3600-3800 μg/ml in the fermentation broth is achieved at termination of the fermentation.

These values are significantly higher than the results obtained by using the methods described in the literature up to the present. According to U.S. Pat. No. 3,067,099 for example a vancomycin content of only 180 μg/ml was achieved in laboratory fermentation; and the active substance content of the fermentation broth was not higher then 200 μg/ml even in fermentations of 1.5 m³ volume, in stirred and aerated equipment at the end of the fermentation.

By using another fermentation process under laboratory contitions a vancomycin content of 950 μg/ml in the fermentation broth was obtained (European patent specification No. 85020435 and U.S. Pat. No. 4,667,024); in a further process 2140 μg/ml was the highest value achieved on an industrial scale in a stirred and aerated fermentor of 120 liters working volume at the end of the fermentation.

The quantitative determination of the antibiotic content of the fermentation broth and final product was performed by using the agar diffusion method according to the prescriptions of USP XXII. on the ATCC 6633 Bacillus subtilis strain. The vancomycin potency values were related to the commercially available USP reference standard.

A HPLC method was used for the qualitative analysis of vancomycin final product [according to: Antimicrobial Agents and Chemotherapy, 27/4, 503/1985); and Code of Federal Register, USA, paragraph 455.85 (1988)].

The fermentations carried out by using the NCAIM 001092 and NCAIM 001093 strains belonging to the *Micropolyspora orientalis* species are illustrated in detail in the following non-limiting Examples.

EXAMPLE 1

The laboratory seed culture-medium with the following composition is inoculated by the vegetative culture of *Micropolyspora orientalis* NCAIM 001092 strain stored in a frozen state between −20° and −30° C.

| | |
|---|---|
| Glucose | 10 g |
| Saccharose | 6 g |
| Soluble starch | 20 g |
| Corn steep liquor | 10 g |
| Soy flour | 14 g |
| Potassium didhydrogen phosphate | 3 g |
| Calcium carbonate | 2 g |
| Solution of mineral salts | 10 ml |
| Distilled water | up to 1000 ml. |

The pH value is 7.2. after sterilization.

To 100 ml of culture-medium 2 ml of vegetative culture is added in an Erlenmeyer flask of 500 ml volume.

Components of the mineral salt solution:

| | |
|---|---|
| Manganous sulfate ($MnSO_4.H_2O$) | 1,0 g |
| Copper sulfate ($CUSO_4.5H_2O$) | 0,1 g |
| Zinc sulfate ($ZnSO_4.7H_2O$) | 2,8 g |
| Iron ammonium citrate | 2,8 g |
| Cobaltous chloride ($COCl_2.H_2O$) | 0,1 g |
| Sodium perborate ($Na_2B_4O_7.H_2O$) | 0,1 g |
| Sodium molybdate ($Na_2MoO_4.H_2O$) | 0,04 g |
| Distilled water | up to 1000 ml. |

The preparation of the laboratory seed culture is performed by cultivating at 30° C. on a gyratory shaker at 180 rpm with a stroke length of 2.5 cm for 20-24 hours. 50 ml of fermentation-medium in an Erlenmeyer flask of 500 ml volume with the following composition are inoculated with 1 ml of the culture obtained above.

| | |
|---|---|
| Glycerol | 60 g |
| Soy flour | 20 g |
| Calcium gluconate | 12 g |
| Potassium dihydrogen phosphate | 0.2 g |
| Magnesium chloride | 0.2 g |
| Calcium carbonate | 3,0 g |
| Tap water | up to 1000 ml. |

After sterilization the pH value is 7.2-7.4.

The fermentation is carried out at 30° C. on a gyratory shaker at 180 rpm with a stroke length of 2.5 cm for 120 hours. At the end of the fermentation the vancomycin content of the fermentation broth is 2800 µg/ml.

EXAMPLE 2

After inoculating the laboratory seed culture-medium described in Example 1 with the vegetative culture of the Micropolyspora NCAIM 001093 strain stored between −25° and −30° C., the preparation of the seed culture and the fermentation are carried out as described in Example 1. At the end of the fermentation a vancomycin content of 2340 µg/ml of the fermentation broth is achieved.

EXAMPLE 3

After inoculating the fermentation culture-medium described in Example 1 by using the process of Example 1, with the inoculum of *Micropolyspora orientalis* NCAIM 001092 strain prepared according to Example 1, sodium nitrate or potassium nitrate is added in a final concentration of 0.6% to the fermentation culture-medium before sterilization. The cultivation is performed as described in Example 1 and a vancomycin content of 3720 µg/ml in the fermentation broth at the end of fermentation is achieved.

EXAMPLE 4

8 liters of inoculum culture-medium described in Example 1 placed in a glass fermenter of 12 liters volume are inoculated with 1 ml of laboratory seed culture of *Micropolyspora orientalis* NCAIM 001092 strain prepared according to Example 1. The cultivation is carried out at 30° C. with an aeration of 6 liters/minute while stirring at 500 rpm for 17-20 hours. 8 liters of sterile fermentation culture-medium placed in a glass fermenter of 12 liters volume with the composition described in Example 3 are inoculated with 800 ml of the culture obtained above. The fermentation is carried out at 30° C. with an aeration of 6 liters/min while stirring at 600 rpm for 120 hours. The vancomycin content of 3820 µg/ml in the fermentation broth at the end of fermentation is achieved.

EXAMPLE 5

An inoculum culture is prepared from *Micropolyspora orientalis* NCAIM 001092 strain as described in Example 1. 100 ml of the above culture are inoculated to 1 m³ of sterile culture-medium in a pre-fermenter of 1.5 m³ volume having the following composition:

| | |
|---|---|
| Corn starch | 20 kg |
| Soy flour | 10 kg |
| Saccharose | 10 kg |
| Calcium carbonate | 2 kg |
| Soy bean oil | 4 kg |
| Polypropylene glycol | 0,5 kg |
| Tap water | up to 1000 litres. |

The pH value of the culture-medium is adjusted by sulfuric acid in such a way that the pH value is 5.5-6.0 after sterilization. The pre-fermentation is carried out at 30° C. with an aeration of 0.5 liter/liter/min under an inner overpressure of 0.4-0.5 bar while stirring at 100 rpm for 17-20 hours. The inoculum thus prepared is introduced to 2 m³ of sterile fermentation-medium prepared in a fermenter of 3 m³ volume with the following composition:

| | |
|---|---|
| Glycerol | 120 kg |
| Soy flour | 40 kg |
| Calcium gluconate | 24 kg |
| Sodium nitrate | 20 kg |
| Calcium carbonate | 8 kg |
| Magnesium chloride | 0,4 kg |
| Potassium dihydrogen phosphate | 0,4 kg |
| Tap water | up to 2000 litres. |

The pH value of the culture-medium is adjusted by adding sodium hydroxide to reach a pH value of 7.0-7.2 after sterilization. The sterile fermentation culture-medium of 2 m³ volume is inoculated with 100 liters of developed industrial seed culture and the fermentation is carried out for 96-120 hours with the following parameters:

| | |
|---|---|
| Temperature | 30° C. |
| Aeration in the 0-17th hours | 0.5 liter/liter/min |
| Aeration from the 17th hour up to termination | 1.0 liter/liter/min |
| Inner pressure | 0.4-0.5 bar |
| Stirring in the 0-17th hours | 50 rpm |
| Stirring from the 17th hour up to termination | 100 rpm. |

At termination of the fermentation the fermentation broth contains 3700 µg/ml of vancomycin which is isolated from the fermentation broth in the following way.

The fermentation broth of 2 m³ volume is cooled to 15° C., diluted with 25 vol % of tap water (calculated on the volume of the fermentation broth) and sodium chloride is added in an amount of 20 g/liter (as calculated for its original volume) under constant stirring and cooling to 15° C. After dissolution of sodium chloride the pH value is adjusted to 8.4-8.6 by adding sodium hydroxide, then 0.4% perlite filter aid is added and the stirring is continued at 15° C. for 2 hours. Then, the fermentation broth thus treated is filtered through a pre-layered vacuum drum-filter of 2 m² surface under reduced pressure and the filtered fermentation broth is collected in a coolable vessel equipped with a stirrer.

From the fermentation broth vancomycine is bound to Amberlite IRC 50 (H+ phase) ion-exchanger resin, 300 liters of which are filled in 2 columns-connected in series (400 mm×2000 mm size). The linear flow rate of binding is 2-3 m/hour. After adsorption the columns are washed with 1500-2000 liters of deionized water at the same linear flow rate as used for binding. Vancomycin is eluated from the columns with 0.5N NH₄OH solution at a linear flow rate of 0.5-1.0 m/hour. During elution fractions of 100 liters are collected, in which the amount and purity of vancomycin are controlled by HPLC examination. The fractions of suitable purity are combined to give 400-600 liters of main fraction. After adjusting the pH value of the combined main fraction to 8.0 by 1N hydrochloric acid, the solution is concentrated up to a vancomycin concentration of 8-12% in a reverse osmosis equipment. During concentrating, the pH value of the solution is gradually adjusted to 5.4-5.6.

For removing the inorganic salts being present in the solution, a so-called diafiltration is performed after concentrating, i.e. the concentrated solution is again diluted with deionized water and concentrated again. At termination of concentrating the volume of the solution is 23-40 liters with a pH value of 5.2-5.4. The pH of the solution is adjusted to 2.5-2.8 by adding 10% hydrochloric acid, then the concentrate is clarified by activated carbon (Carbo C Extra carbon). An amount of 2§% carbon calculated for the vancomycin content (determined by HPLC) is used for each clarification. If the colour of the solution, measured spectrophotometrically in an 1-cm cuvet at 380 nm, is higher than A=0.4, the clarification is repeated as described above.

Subsequently, the clarified clear solution is passed through a Diaion SK 1B (H+ phase) strongly acidic, cation-exchanger column. A column of 120 mm in diameter filled with 4 liters of resin is used with a linear flow rate of 8 m/hour. Vancomycin is washed with distilled water from the column. The pH value of the solution obtained, which is between 1.8 and 2.0 after the cation-exchanging step, is adjusted to 3.0-3.5 by passing it through a column of 2 liters volume and 120 mm in diameter containing a weakly basic anion-exchanger resin (OH− phase) at a flow rate of 6 m/hour. The column is washed with distilled water and the washing solution containing vancomycin is combined with the main fraction. The solution obtained is filtered through an ultrafilter membrane (Millipore Pellicon device) with exclusion of 30000 nominal molecular weight. From the ultrafiltered solution with a volume of 30–40 liters vancomycin is precipitated with a 11-fold volume of sterile-filtered acetone, then dried at 40°-50° C. under sterile conditions in an oven under reduced pressure for 20 hours and finally powdered. From 2 $m^3$ of starting fermentation broth 2873 g of vancomycin hydrochloride are obtained with a biological potency of higher than 968 μg/mg based on microbiological determination.

We claim:

1. A microbial process for the fermentative preparation of the antibiotic vancomycin which comprises 1) culturing a *Micropolyspora orientalis* aminoglycoside-resistant strain selected from the group consisting of NCAIM B/P/001092 and NCAIM B/P/001093, or progeny strains thereof, on a nutrient medium containing assimilable carbon and nitrogen sources, and mineral salts as nitrate at a concentration of 0.1 to 2.5% (w/v), under aerobic conditions, at 25° to 30° C., until the antibiotic is produced, and 2) recovering said vancomycin antibiotic.

2. The process of claim 1, wherein the culture medium contains soy flour, glycerol, calcium gluconate, corn starch, and sodium and/or potassium nitrate.

* * * * *